United States Patent [19]
Koveal et al.

[11] Patent Number: 5,929,126
[45] Date of Patent: Jul. 27, 1999

[54] GAS CONVERSION WITH REJUVENATION AMMONIA REMOVAL

[75] Inventors: Russel J. Koveal, Baton Rouge, La.; Dennis G. Alexion, Succasunna, N.J.

[73] Assignee: Exxon Research and Engineering Co., Florham Park, N.J.

[21] Appl. No.: 09/016,178

[22] Filed: Jan. 30, 1998

[51] Int. Cl.⁶ .............................. C07C 27/00; C07C 1/02; C01C 3/00
[52] U.S. Cl. ...................... 518/709; 518/702; 518/700; 518/715; 252/373; 423/236
[58] Field of Search ................................ 518/709, 702, 518/700, 715; 252/373; 423/236

[56] References Cited

U.S. PATENT DOCUMENTS

| | | | |
|---|---|---|---|
| 4,189,307 | 2/1980 | Marion | 48/197 |
| 4,769,224 | 9/1988 | van Grinsven et al. | 423/236 |
| 5,068,254 | 11/1991 | Posthuma et al. | 518/705 |
| 5,260,239 | 11/1993 | Hsia | 502/30 |
| 5,283,216 | 2/1994 | Mitchell | 502/30 |

FOREIGN PATENT DOCUMENTS

| | | | |
|---|---|---|---|
| 0661372 | 7/1995 | European Pat. Off. | C10K 1/10 |
| 0661375 | 7/1995 | European Pat. Off. | C10K 1/34 |

*Primary Examiner*—Paul J. Killos
*Assistant Examiner*—J. Parsa
*Attorney, Agent, or Firm*—Jay Simon

[57] ABSTRACT

A gas conversion process includes producing a synthesis gas which contains ammonia and hydrogen cyanide and forms hydrocarbons by reacting the hydrogen and carbon monoxide in the gas in the presence of a hydrocarbon synthesis catalyst also reversibly deactivates the catalyst due to the presence of the ammonia and hydrogen cyanide in the gas. The catalyst is rejuvenated with a gas comprising hydrogen and produces an ammonia containing rejuvenation offgas. The ammonia is dissolved out of the offgas with water and then stripped out of the water with the hydrocarbon feed to the synthesis gas generator and into the generator where it is consumed.

16 Claims, 1 Drawing Sheet

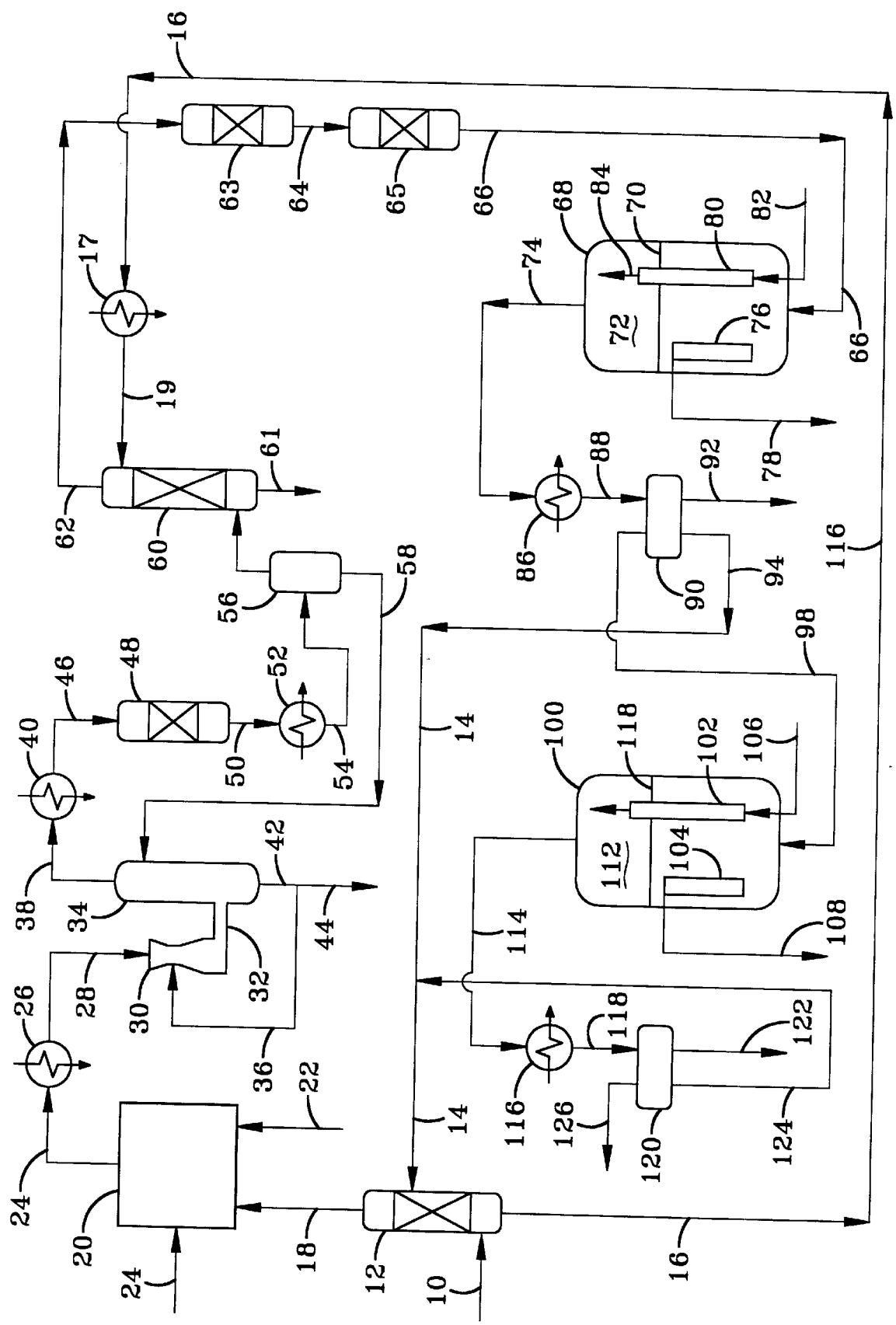

GAS CONVERSION WITH REJUVENATION AMMONIA REMOVAL

BACKGROUND OF THE DISCLOSURE

1. Field of the Invention

The invention relates to an environmentally friendly gas conversion process which produces and disposes of ammonia in the process. More particularly, the invention relates to a gas conversion process which includes (i) synthesis gas generation, (ii) hydrocarbon synthesis and (iii) catalyst rejuvenation which produces ammonia containing gas, from which the ammonia is removed with water and disposed of by using the hydrocarbon gas feed to the synthesis gas generator to strip it out of the water and into the generator, where it is consumed.

2. Background of the Invention

Hydrocarbon synthesis (HCS) processes are well known and include fixed bed, fluid bed and slurry type processes in which a synthesis gas (syngas) comprising a mixture of $H_2$ and CO is reacted in the presence of a suitable Fischer-Tropsch type of hydrocarbon synthesis catalyst at conditions effective to form hydrocarbons, and preferably $C_{5+}$ hydrocarbons which are solid at standard room temperature conditions of temperature and pressure. The syngas is produced by reacting a low molecular weight hydrocarbon gas with oxygen and steam, via well known processes which include partial oxidation with or without a catalyst, catalytic steam reforming and combination thereof, using a fixed or fluid catalyst bed. Syngas made from hydrocarbon gas which contains nitrogen (i.e., natural gas) or nitrogen containing compounds (i.e., the hydrocarbon gas is derived from a resid, coal, shale, coke, tar sands, etc.) invariably contains nitrogen species (e.g., HCN and $NH_3$ which deactivate the HCS catalyst. This deactivation may be reversed and catalytic activity restored (rejuvenated) by contacting the deactivated catalyst with hydrogen or a hydrogen containing gas (rejuvenating gas) as is disclosed, for example, in U.S. Pat. No. 5,260,239. The rejuvenation produces ammonia which must be removed from the gas and disposed. U.S. Pat. Nos. 4,189,307; 4,769,224 and 5,068,254 and European patent publications EP 0 661 372 A and EP 0 661 375 A disclose methods for removing ammonia and cyanide from syngas, including recycle of ammonia containing gas and water back into the syngas generator, but do not address a gas conversion process which includes removal and disposal of ammonia from an HCS catalyst rejuvenation offgas.

SUMMARY OF THE INVENTION

The invention relates to a gas conversion process which includes (i) synthesis gas (syngas) generation, (ii) hydrocarbon synthesis (HCS) and (iii) rejuvenation of the HCS catalyst which produces an ammonia containing gas, from which the ammonia is removed with water and disposed of, by using the hydrocarbon gas feed for the syngas production to strip it out of the water and into the syngas generator where it is consumed. Even very minor amounts (e.g., <10 vppb) of reversible HCS catalyst deactivating nitrogen species, such as ammonia and hydrogen cyanide, will result in loss of the activity of the HCS catalyst for hydrocarbon production over time, thereby requiring restoration of the catalytic activity by contacting it with a gas comprising hydrogen (hereinafter "rejuvenation"). This rejuvenation requires hydrogen and produces a rejuvenation product gas (hereinafter "offgas") which contains ammonia. The ammonia is removed from the gas with water to form an aqueous ammonia solution which is separated from the ammonia reduced offgas and contacted with the hydrocarbon gas being fed into the syngas generator. The hydrocarbon gas strips the ammonia out of the water and carries it into the equilibrium controlled syngas generator in which it is consumed. This also humidifies the hydrocarbon gas feed and produces clean water which may be recycled back into the gas conversion process and used for various purposes, such as scrubbing the syngas, or disposed. Water for removing the ammonia from the offgas is obtained by cooling the gas produced by the HCS reaction (hereinafter "tail gas") which contains a significant amount of water vapor produced by the HCS reaction.

More specifically, the invention comprises a gas conversion process including syngas production, catalytic hydrocarbon synthesis and rejuvenation of the hydrocarbon synthesis catalyst, wherein the process comprises: (a) producing, from a hydrocarbon gas in a syngas generator, a syngas comprising a mixture of $H_2$ and CO which also contains at least one of ammonia and hydrogen cyanide; (b) contacting the syngas with a hydrocarbon synthesis catalyst and reacting the $H_2$ and CO in the presence of the catalyst at reaction conditions effective to form hydrocarbons and reversibly deactivate the catalyst; (c) contacting the reversibly catalyst with a gas comprising hydrogen to rejuvenate it and produce a rejuvenation offgas containing ammonia; (d) contacting the offgas with water to dissolve the ammonia and form an aqueous ammonia solution and separating the solution from the offgas, and (e) stripping the ammonia out of the solution with the hydrocarbon gas feed to the syngas generator and passing it into the generator. While either hydrogen cyanide or ammonia reversibly deactivate the HCS catalyst, ammonia is produced during the rejuvenation. The HCS catalyst is rejuvenated either in-situ in the HCS reactor or ex-situ in an external vessel by contacting it with a gas which comprises hydrogen, as is known. Further, the offgas may or may not be combined with the HCS reaction tail gas. The rejuvenating offgas typically contains enough water to dissolve out most of the ammonia from the gas, with the actual amount of ammonia removal depending on the water temperature. The syngas generator is equilibrium controlled with respect to formation of the ammonia and hydrogen cyanide catalyst deactivating species. Therefore, feeding the ammonia into the syngas generator shifts the equilibrium conditions in the generator towards nitrogen formation and this in effect removes the ammonia, by limiting it to the equilibrium amount present in the generator, and therefore in the syngas. In the practice of the invention it is preferred that the sulfur content of the hydrocarbon gas feed to the syngas generator be reduced by removing most of the sulfur from the gas feed before it strips the ammonia out of the water and enters the syngas generator. It is preferred that the sulfur content of the gas be less than 1 vppm of sulfur, more preferably less than 0.1 vppm and still more preferably less than 50 vppb. The concentration of the combined total of hydrogen cyanide and ammonia present in the syngas is preferably reduced to less than 0.1 vppm, more preferably less than 50 vppb and still more preferably less than 20 vppb before the syngas contacts the HCS catalyst.

BRIEF DESCRIPTION OF THE DRAWING

The FIGURE is a schematic block flow diagram of an embodiment of the process of the invention.

DETAILED DESCRIPTION

During Fischer-Tropsch hydrocarbon synthesis (HCS), the HCS catalyst loses activity (deactivates) due to contact with either or both of the $NH_3$ and HCN deactivating species present in the syngas and which result from the synthesis reaction. Even very small amounts of less than 50 vppb of either or both of these species causes catalyst deactivation and concomitant reduction of hydrocarbon productivity. Deactivation occurs irrespective of whether the HCS reaction is conducted in the presence of a fixed or fluid bed of catalyst, or if it is conducted in a slurry. This deactivation is reversible and catalytic activity is restored (the catalyst rejuvenated) by contacting the deactivated catalyst with hydrogen or a gas comprising hydrogen, as is known. The activity of the HCS catalyst is either intermittently or continuously rejuvenated, either in-situ in an HCS reactor or in an external rejuvenation vessel, as is disclosed, for example, in U.S. Pat. Nos. 5,260,239; 5,268,344, and 5,283,216. Catalyst rejuvenation will occur under the same conditions of temperature and pressure as the HCS reaction given below. The '239 patent gives typical hydrogen partial pressures, treat rates, etc. for the rejuvenation. The rejuvenating gas may contain diluents and even minor amounts of CO, provided that the hydrogen concentration is sufficient to consume any CO that may be present during the rejuvenation and to insure that the offgas produced by the rejuvenation contains unreacted hydrogen. It is believed that the rejuvenated catalyst should remain in contact with hydrogen to prevent deactivation. Deactivation caused by loss of contact with hydrogen is not fully reversible. The rejuvenation produces an offgas which contains ammonia and this ammonia must be disposed of. The process of the invention provides a convenient and facile means for disposing of the ammonia by passing it into the equilibrium controlled syngas generator.

In the process of the invention, the syngas which comprises a mixture of $H_2$ and CO is formed from a hydrocarbonaceous gas feed. While the hydrocarbon gas feed for the syngas generator is conveniently derived from natural gas which comprises mostly methane, it may be obtained by any available and convenient means from any suitable hydrocarbonaceous material. Typically an HCS plant will be proximate a source of such hydrocarbonaceous materials and the syngas generating operation will be an integral part of the HCS plant. Feeds comprising a low molecular weight (e.g., $C_1$–$C_4$) hydrocarbon gas, preferably alkane and more preferably mostly methane, as in natural gas are preferred. Natural gas is particularly preferred because it comprises primarily methane, is convenient, clean and doesn't leave large quantities of ash, shale, sulfur compounds and the like to be handled and disposed of Irrespective of either the source of the hydrocarbon gas for the syngas production or the process, such hydrocarbon feeds invariably contain elemental nitrogen or nitrogen containing compounds which react in the syngas generator to form nitrogenous species, such as HCN and $NH_3$, which deactivate the HCS catalyst during the HCS reaction. After sulfur and, if necessary, $CO_2$ removal, the natural gas is fed into a syngas generator in which the hydrocarbon component of the gas is reacted with oxygen or air and, optionally steam, to form the syngas comprising a mixture of $H_2$ and CO in the desired mole ratio. As is known, syngas may be formed by non-catalytic and catalytic partial oxidation, steam reforming and combination of partial oxidation and reforming. In catalytic partial oxidation, a premixed feed of hydrocarbon gas, oxygen, and optionally steam or water vapor, is reacted in the presence of a noble metal catalyst and preferably a supported noble metal catalyst in the syngas generator to form the syngas, as is known. Processes that combine partial oxidation and steam reforming may have the steam reforming catalyst in either a fixed or fluid bed, with a fluid bed having superior mixing and heat transfer characteristics. In a fluid bed syngas generating (FBSG) process, the partial oxidation and steam reforming both occur in the presence of the fluidized steam reforming catalyst. FBSG is disclosed, for example, in U.S. Pat. Nos. 4,888,131 and 5,160,456. In autothermal reforming, partial oxidation occurs in the absence of a catalyst and precedes adiabatic steam reforming which occurs in a fixed bed of catalyst. The syngas exiting the reactor comprises a mixture of $H_2$ and CO along with water vapor or steam, nitrogen, $CO_2$, minor amounts of unreacted methane, $NH_3$ and HCN. The amount of $CO_2$ present in the feed to the syngas generator will effect the reaction equilibrium and may be used, along with the conditions in the unit, to adjust the $H_2$ to CO ratio of the syngas. Most of the water is removed from the syngas before it is passed into an HCS reactor. The syngas generator reactor is equilibrium controlled with respect to the amount of HCN and $NH_3$ present in the generator or reactor, which can be illustrated by the following reactions:

$$N_2 + 3H_2 \Leftrightarrow 2NH_3$$

$$N_2 + 2CH_4 \Leftrightarrow 2HCN + 3H_2$$

$$NH_3 + CO \Leftrightarrow HCN + CO_2$$

Therefore, disposal of the HCN and $NH_3$ catalyst deactivating species occurs when these compounds are fed into the equilibrium limited syngas generator, by shifting the reactions back towards nitrogen.

In an HCS process, liquid and gaseous hydrocarbon products are formed by contacting a syngas comprising a mixture of $H_2$ and CO with a Fischer-Tropsch type of HCS catalyst, under shifting or non-shifting conditions and preferably under non-shifting conditions in which little or no water gas shift reaction occurs, particularly when the catalytic metal comprises Co, Ru or mixture thereof. Suitable Fischer-Tropsch reaction types of catalyst comprise, for example, one or more Group VIII catalytic metals such as Fe, Ni, Co, Ru and Re. In one embodiment the catalyst comprises catalytically effective amounts of Co and one or more of Re, Ru, Fe, Ni, Th, Zr, Hf, U, Mg and La on a suitable inorganic support material, preferably one which comprises one or more refractory metal oxides. Preferred supports for Co containing catalysts comprise titania, particularly when employing a slurry HCS process in which higher molecular weight, primarily paraffinic liquid hydrocarbon products are desired. Useful catalysts and their preparation are known and illustrative, but nonlimiting examples may be found, for example, in U.S. Pat. Nos. 4,568,663; 4,663,305; 4,542,122; 4,621,072 and 5,545,674.

With respect to the hydrocarbon synthesis, fixed bed, fluid bed and slurry hydrocarbon synthesis (HCS) processes for forming hydrocarbons from a syngas comprising a mixture of $H_2$ and CO are well known and documented in the literature. In all of these processes the $H_2$ and CO in the syngas are reacted in the presence of a suitable Fischer-Tropsch type of hydrocarbon synthesis catalyst, at reaction conditions effective to form hydrocarbons. Some of these hydrocarbons will be liquid, some solid (e.g., wax) and some gas at standard conditions of temperature and pressure of 25° C. and one atmosphere, particularly if a catalyst having a catalytic cobalt component is used. Slurry HCS processes are often preferred because of their superior heat (and mass) transfer characteristics for the strongly exothermic synthesis reaction and because they are able to produce relatively high molecular weight, paraffinic hydrocarbons when using a cobalt catalyst. In a slurry HCS process a syngas comprising a mixture of $H_2$ and CO is bubbled up as a third phase through a slurry in a reactor which comprises a particulate Fischer-Tropsch type hydrocarbon synthesis catalyst dispersed and suspended in a slurry liquid comprising hydrocarbon products of the synthesis reaction which are liquid at the reaction conditions. The mole ratio of the hydrogen to the carbon monoxide may broadly range from about 0.5 to 4, but is more typically within the range of from about 0.7 to 2.75 and preferably from about 0.7 to 2.5. The stoichiometric mole ratio for a Fischer-Tropsch HCS reaction is 2.0, but in the practice of the present invention it may be increased to obtain the amount of hydrogen desired from the syngas for other than the HCS reaction. In a slurry HCS process the mole ratio of the $H_2$ to CO is typically about 2.1/1. Slurry HCS process conditions vary somewhat depending on the catalyst and desired products. Typical conditions effective to form hydrocarbons comprising mostly $C_{5+}$ paraffins, (e.g., $C_{5+}-C_{200}$) and preferably $C_{10+}$ paraffins, in a slurry HCS process employing a catalyst comprising a supported cobalt component include, for example, temperatures, pressures and hourly gas space velocities in the range of from about 320–600° F., 80–600 psi and 100–40,000 V/hr/V, expressed as standard volumes of the gaseous CO and $H_2$ mixture (0° C., 1 atm) per hour per volume of catalyst, respectively.

Referring to the FIGURE, preheated natural gas processed by amine treating and absorption to remove sulfur and $CO_2$, substantially sulfur-free (e.g., <0.1 vppm), and containing about 4% nitrogen is passed via line 10 into the bottom of a gas-liquid contacting tower indicated as vessel 12, in which it is contacted with water entering near the top of the tower via line 14. Tower 12 is filled with inert packing material such as rashig rings, berl saddles, structured packing and the like, or contain a plurality of trays to insure sufficient contact for the gas to contain enough water vapor for the syngas generation downstream. The contacting is typically sufficient to saturate the gas with water vapor. The water entering the tower is HCS reaction water recovered from the tail gas of the HCS reactors 68 and 100 which contains the ammonia produced by the catalyst rejuvenation and also other water soluble compounds (e.g., oxygenates such as acids, alcohols, aldehydes and the like) produced by the HCS reaction. In the embodiment shown, the catalyst is rejuvenated in-situ which produces the offgas containing the ammonia, while the reactors are producing hydrocarbons. As shown, in this embodiment the rejuvenation offgas is combined with the HCS reactor tail gas and the combined stream cooled to condense out at least a portion of the water and with it the ammonia and other water soluble compounds and form the ammonia solution which is passed into the FBSG. These water soluble compounds are stripped from the downflowing water by the upflowing natural gas stream and passed into the syngas generator with the gas, in which they are destroyed by the heat and equilibrium controlled conditions in the generator, and thereby effectively disposed of. The resulting water stripped of these water soluble compounds, and which has been defined above as clean water, passes out the bottom of the vessel via line 16 and through heat exchanger 17 in which it is cooled and then into scrubber 60, via line 19, in which it is contacted with the hydrolyzed syngas from which most of the HCN and $NH_3$ have been removed, as a polishing or finishing step to remove any HCN and $NH_3$ remaining in the gas down to a level of less than 50 vppb and preferably less than 10 vppb. At least 95%, preferably at least 98% and more preferably at least 99% of the ammonia and any remaining hydrogen cyanide are stripped out of the water to produce clean water. This water will typically contain less than 100 mg/L of ammonia and less than 1 mg/L (e.g., 0–<1 mg/L) of hydrogen cyanide. Optionally, a reboiler (not shown) located either in the bottom of tower 12 or external of it, as is known to those skilled in the art, may be used to heat a portion of the clean water to produce steam, if required to insure the desired degree of humidification of the hydrocarbon feed stripping gas. This steam will pass up through the tower with the hydrocarbon feed gas. The water saturated natural gas is passed, via line 18, from the humidifier-stripper 12 into syngas generator 20. The syngas generator may comprise more than one vessel as is known to those skilled in the art. It may, for example, be a fluid bed syngas generator (FBSG), an autothermal generator, a partial oxidation unit and may have a fixed bed of catalyst following a fluidized catalyst bed as is disclosed in U.S. Pat. No. 5,421,850. A discussion of the relative merits of these units is discussed, for example, in U.S. Pat. Nos. 3,441,370 and 5,244,641. In an FBSG, the partial oxidation takes place in the presence of the fluidized bed of steam reforming catalyst particles. A typical steam reforming catalyst comprises a catalytic nickel component supported on alpha alumina as is disclosed in U.S. Pat. No. 5,395,406. The FBSG has superior heat transfer characteristics and the fluidized catalyst bed may also contain particles of high temperature, heat resistant material, such as alpha alumina, as is known. For the purposes of this illustration, the syngas generating unit 20 will be taken as an FBSG unit. Typical conditions in an FBSG include pressures in the range of about 10–50 atmospheres, preferably 10–40 atmospheres and more preferably 20–40 atmospheres, while the temperature will range to within about 50° F. of the softening point of the, essentially non-catalytic, heat carrying particles, preferably from about 1650° F. to about 2000° F. and more preferably from about 1700° F. to about 1800° F. If necessary, additional water vapor or steam is fed into the FBSG via line 22 and oxygen or an oxygen containing gas (e.g., air, oxygen diluted with $N_2$ or steam, etc.), and preferably oxygen, is fed into the FBSG via line 24. In the FBSG the hydrocarbons in the natural gas, which comprise mostly methane and typically along with minor amounts of $C_2$–$C_8$ hydrocarbons, are partially oxidized and catalytically steam reformed to produce a syngas comprising a mixture of $H_2$ and CO. The ammonia stripped out of the water enters the FBSG where its concentration is adjusted by the equilibrium conditions, thereby effectively disposing of the ammonia. The organics stripped from the humidifying water in 12 are also destroyed in the generator. Due to the high temperature in the syngas generator, the syngas exiting the unit via line 24, after passing through primary and secondary cyclones (not shown), is optionally passed through a heat exchanger 26 (or through a turbine for generating electricity), which could be a steam generator, which cools it to a temperature of less than 1,000° F., and then, via line 28, into a high energy gas-water contacting means, which in this illustration is venturi scrubber 30. If the heat exchanger is not used, the gas is cooled by contact with the water in the scrubber. Venturi scrubbers are well known and need not be explained. Other types of high energy contacting means include cyclone scrubbers, impingement plate scrubbers, mechanical scrubbers such as a Roto-Clone (American Air Filter Co.), and the like. The syngas contains small amounts of particulate matter entrained from the FBSG (e.g., catalyst and heat transfer solids fines) and, as it passes down through the venturi scrubber, it is contacted with water entering the venturi via line 36, which further cools the gas down to about 300–400° F. and also removes the particulate matter from the gas. The scrubbed gas and the water which contains the particulate matter are passed into a separator-demister 34, via conduit 32, in which the fines containing water is separated from the gas. Crinkled wire, wire mesh, loose packing and the like in the upper portion (not shown) of the device detrains the particulate-containing mist formed in the venturi scrubber, which coalesces into particulate containing water which combines with the bulk particulate containing water entering the device from the scrubber. Ammoniated water withdrawn from separator 56 via line 58 enters the top of 34 and flows down through the demisting means therein, wherein it contacts the coalescing mist and upflowing gas to ensure that the gas is particle-free prior to leaving the separator-demister. Optionally, all or a portion of the water entering the top of 34 may come from scrubber 60 via line 61 and which contains very little dissolved HCN and $NH_3$. The particulate free and demisted syngas is removed from the separator-demister via line 38 and passed into another heat exchanger 40, in which it is heated or cooled down to about 400° F. for the subsequent catalytic hydrolysis step. The water phase is withdrawn from vessel 34 via line 42 and a portion recycled back into the venturi scrubber via line 36, with the remainder sent via line 44 to disposal. Optionally, a portion of the water passed into the venturi scrubber may comprise the ammoniated water separated in 56 or water from scrubber 60. The cool gas exiting the heat exchanger is passed into a hydrolysis reactor 48 via line 46. This reactor contains a hydrolysis zone which comprises a fixed bed of catalyst for hydrolyzing the HCN to $NH_3$. The catalyst in the HCN hydrolysis zone preferably comprises an oxide of at least one metal selected from the group consisting essentially of a Group VI metal, a Group IVB metal and mixture thereof and particularly an oxide of Al and at least one of Mo and Ti as is disclosed in European patent publication EP 0 757 969 A. The catalyst will comprise a composite oxide of from about >0 to 30 wt. % Mo as the oxide, preferably 10 to 20 wt. %, with the titania present in an amount of about >0 to 30 wt. %, preferably 4 to 20 wt. %, more preferably 8–16 wt. % (e.g., 8 wt. %), with the remainder being alumina. The catalyst may be readily prepared by depositing suitable sources of molybdenum and titanium on an alumina support and after deposition by, for example, impregnation or incipient wetness techniques, the composite is dried and then calcined at temperatures of from about 250–500° C., and preferably 350–450° C. to produce the oxide form. It is preferred that the catalyst be treated with hydrogen at a temperature of from about 200–600° C., preferably 230–550° C. for from 1–24 hours. The alumina may be any alumina useful as a catalyst support and typically one having a surface area of between about 100–400 m²/g. The amount of HCN to be hydrolyzed and removed from the synthesis gas is typically very small (e.g., <5000 vppb). Water typically present in an amount of from about 5–25 volume % results from the syngas generation, although the actual amount of water present may be greater or lower, and this amount of water is more than sufficient to hydrolyze the relatively minor amount of HCN present in the syngas. During the hydrolysis reaction, the HCN reacts with water and is converted to $NH_3$ and CO. At least about 95%, typically at least 98% and even more than 99% of the HCN is converted to $NH_3$. A natural gas comprising about 96% methane and 4% nitrogen which is catalytically partially oxidized and steam reformed in an FBSG operating at about 1800° F. and 400 psia, will produce a syngas having an equilibrium limited amount of HCN and $NH_3$ of about 5 ppm and 300 ppm, respectively. Some $NH_3$ and a minor portion of the HCN are removed from the gas by the water in the venturi scrubber. The temperature, pressure and space velocity in the HCN hydrolysis zone 48 may broadly range from about 100–400° C., 1–100 atm and 2000–50000 GHSV. The hydrolysis temperature is chosen so as to achieve a hydrolysis rate sufficient to achieve at least 95%, preferably at least 98% and still more preferably at least 99% conversion of the HCN to $NH_3$ in the hydrolysis reactor, depending on the level of the HCN in the gas and the hydrolysis temperature in the reactor, while avoiding undesirable side reactions such as methanation of the CO present in the syngas. The hydrolyzed syngas passes out of the reactor 48 via line 50, and then through a heat exchanger 52, in which it is cooled to about 120° F. which condenses out most of the water vapor in the gas and with it, the $NH_3$. The liquid water resulting from this condensation contains most (e.g., 90%) of the $NH_3$ that was present, leaving very little left in the gas. In one experiment, syngas containing on a volume % basis, 43% $H_2$, 21.2% CO, 7% $CO_2$, 8.6% $N_2$, 5.4% $CH_4$, 15% $H_2O$, 340 vppm $NH_3$ and 6.4 vppm HCN was passed through an HCN hydrolysis zone at 205° C., 26.4 atm., and 12000 hr-1 space velocity, in which it contacted an HCN hydrolysis catalyst which comprised an alumina and titania support material which was impregnated with ammonium heptamolybdate and calcined as outlined above. The HCN concentration in the syngas exiting the reactor was less than 20 vppb which represented more than 99% removal of the HCN. A repeat of this experiment using more sensitive analytical procedures revealed it to be less than 10 vppb. The hydrolysis reactor was operated for 127 days with no measurable decrease in HCN removal activity. In another experiment, identical to the experiment above, but wherein the temperature in the hydrolysis reactor was at 165° C., the concentration of HCN in the exiting syngas was 269 vppb, indicating 95.8% conversion of HCN in the reactor. After hydrolysis and water scrubbing, the syngas may be passed through one or more beds containing HCN and $NH_3$ adsorbents such as alumina or activated carbon, if for no other reason than to guard the downstream HCS reactor from break throughs in HCN and $NH_3$ concentration in the syngas. While catalytic hydrolysis of the HCN to $NH_3$ is shown in this preferred embodiment, catalytic hydrogenation of the HCN to $NH_3$ may also be employed as is disclosed, for example, in European patent publication EP 0 767 137 A and UK patent application GB 2 267 048 A.

The gas and ammonia water formed in the heat exchanger are then passed into a gas-liquid separator 56 which may be a simple knock-out drum, via line 54, in which the aqueous ammonia solution is separated from the gas and passed, via line 55, back into vessel 34 as wash water. The advantage of converting the HCN into $NH_3$ is that $NH_3$ is extremely water soluble, whereas the HCN is not soluble enough in water to remove it from the gas down to the desired levels. In fact, quantitative removal of $NH_3$ by water washing is easily achieved. Depending on the water temperature and the wash rate, only about 25% of the HCN dissolves in the water. With the natural gas feed to the syngas generator and the hydrolysis catalyst and conditions described above, the amount of HCN remaining in the syngas after hydrolysis is <20 vppb. The syngas is passed from the separator 56, via line 58, to a scrubber 60 which is a cap and tray column, a packed tower containing high surface area packing such as rashig rings, and the like. Wash water, which is the clean water recovered from vessel 12, cooled to a temperature of about 50° C. by passing through indirect heat exchanger 17, enters the top of the scrubber via line 19 and flows down thereby contacting the upward flowing syngas and dissolving substantially all of the ammonia in the gas to produce a scrubbed syngas having an $NH_3$ content less than 20 vppb and preferably less than 10 vppb of $NH_3$, and about 10 vppb of HCN. While in this example the scrubber operates at 20° C., it may be operated at a temperature of from about 25–120° C. The effluent water containing the removed $NH_3$ is removed from the scrubber via line 33 and disposed of in any convenient manner, including recycle back to the syngas generating step, the separator-demister, the high energy contacting means, stripping out the $NH_3$ with nitrogen or fuel gas and combining it into a fuel stream, or by biological treatment. The scrubbed syngas leaves the scrubber via line 62 and is passed into an adsorption zone indicated by vessel 64, in which it contacts one or more solid adsorbents which are selective for adsorption of HCN and $NH_3$ in the presence of CO, $CO_2$, $H_2$ and $H_2O$, illustrative, but nonlimiting examples of which include zeolite molecular sieves, activated carbon, ZnO, alumina and the like, with activated alumina and activated carbon being preferred. The adsorption of the residual HCN and $NH_3$ is carried out at temperatures of from 25 to 120° C., pressures of from 1 to 100 atm and space velocities of from about 2000 to 20000 scf/hr. The syngas resulting from this adsorption step will contain less than 50, preferably less than 20 and more preferably less than 10 vppb of the combined total amount of HCN and $NH_3$ and is suitable for Fischer-Tropsch hydrocarbon and methanol synthesis. However, in this embodiment, after exiting 64 via line 63, the gas passes through a sulfur absorber 65 which contains a suitable sulfur absorbent such as zinc oxide which removes sulfur compounds from the gas down to a level of less than 50 vppb and more preferably less than 10 vppb. This produces a clean syngas essentially free of HCN, $NH_3$ and sulfur which may then be used for Fischer-Tropsch synthesis with reduced catalyst deactivation.

In the embodiment in the FIGURE, this syngas is then passed via line 66 into the bottom of a first stage slurry hydrocarbon synthesis reactor 68, via gas distribution means (not shown) at the bottom of the slurry (not shown), the top of which is indicated at 70. In the reactor, the syngas rises up into the slurry as gas bubbles, and the $H_2$ and CO react in the presence of particles of a solid, particulate Fischer-Tropsch catalyst suspended or dispersed in the slurry to produce hydrocarbons, at least a portion of which are liquid at the reaction conditions. The HCS reaction also produces water vapor (steam), $CO_2$ and some hydrocarbons which are gas at the reaction conditions. The synthesized hydrocarbons which are liquid at the reaction conditions comprise the slurry liquid and are separated from the catalyst particles and withdrawn from the reactor by suitable means, such as one or more liquid filters briefly indicated as box 76, and passed out of the reactor via line 78 to upgrading. The minute levels of the catalyst deactivating species in the syngas results in the production of very pure hydrocarbon liquids which are easily fractionated and upgraded by one or more hydroconversion operations, without the need for the processing required if such compounds are present. This is because hydroprocessing catalysts are poisoned by nitrogen compounds, which means that if such compounds are present, the hydroprocessing has to be conducted at higher temperatures and pressures which are more selective to gas make and less selective to the desired liquid products, than lower temperatures and pressures. The gaseous reaction products, which comprise significant amounts of water vapor as steam, along with unreacted syngas, pass up through the slurry, into the gas space 72 above the slurry and out of the reactor via line 74 as tail gas. An HCS catalyst rejuvenation means 80, such as a conduit open at both ends disclosed in the prior art, is immersed in the slurry with the top extending up into gas space 72. A gas line 82 injects an HCS catalyst rejuvenating gas comprising hydrogen up into the interior of the means 80. The uprising rejuvenation gas acts as a lift gas creating slurry circulation up through and out of the means and at the same time rejuvenates the deactivated catalyst particles which rise up with the uprising slurry, out of the top, and back into the main slurry body in the reactor. The catalyst rejuvenation creates an ammonia-containing offgas which rises up and out of the rejuvenation means, into gas space 72 indicated by arrow 84 and out of the reactor via line 74, along with the gaseous HCS reaction products as part of the reactor tail gas. This tail gas is passed, via line 74, through an indirect heat exchanger 86 which cools the gas, thereby condensing some of the gaseous hydrocarbons as a hydrocarbon liquid and most of the water vapor resulting from the HCS reaction as liquid water which contains the catalyst deactivating species and oxygenates. The mixture of remaining tail gas, hydrocarbon liquid and reaction water, at a temperature ranging from about 100–300° F., is passed, via line 88 from the heat exchanger to a knock-out drum or separation vessel 90. In vessel 90 the liquids separate from the gas and form two layers, one layer being the condensed HCS reaction water which now contains the ammonia and other water soluble compounds and the other layer the condensed hydrocarbon liquid. The hydrocarbon liquid is withdrawn from the separation vessel via line 92 and sent to further processing and upgrading operations. The aqueous solution containing the ammonia and oxygenates is passed, via lines 94 and 14, into vessel 12 in which it is contacted with the natural gas stream which strips the ammonia and oxygenates out of the water to form clean water and carries them into the syngas generator 20 in which they are consumed. The clean water resulting from the stripping is then passed, via line 16, etc., into gas-liquid contacting vessel 60 in which it dissolves substantially all of the remaining catalyst deactivating species (e.g., ammonia) from the syngas. If rejuvenation is conducted in a vessel separate from the HCS reactor, the rejuvenation offgas is combined with the HCS reactor tail gas and sent through the heat exchanger and into the gas-liquid separation vessel. At least one stage of indirect heat exchange cooling followed by gas-liquid separation is employed to treat the tail gas from each of the HCS reactor stages as shown. However, two or more cooling stages may be used. For example, if two stages are employed, the temperature of the cooled liquids and gas in the second stage will be lower than that in the first stage, with the aqueous solution recovered from each stage combined and fed into vessel 12. The first stage HCS reactor is operated at less than 100% CO conversion (e.g., ~80%), so that the first stage tail gas containing unreacted $H_2$ and CO and reduced in water, hydrocarbon liquids, ammonia and other water soluble compounds is passed, via line 98, to the second HCS reactor 100. Thus, the purified first stage tail gas is the feed for the second stage HCS reactor and is passed up into the slurry in the second stage reactor 100 by the same manner and means as for the first stage reactor 68. Optionally, a compressor and $CO_2$ removal means (not shown) may be placed in line 98 between separator 90 and the second stage reactor. Reactor 100 also has a rejuvenation conduit or means 102 and liquid filter 104 similar to those in the first stage reactor, with gas line 106 introducing the HCS catalyst rejuvenating gas into the rejuvenation means and filtrate line 108 passing the hydrocarbon liquid removed from the slurry to further processing and upgrading by one or more conversion operations. The gaseous products of the HCS reaction and of the catalyst rejuvenation pass up into gas space 112 and are removed from the reactor 100 as second stage tail gas via line 114. This tail gas is passed to at least one stage of cooling and gas-liquid separation in the same manner as for the first stage HCS reactor. Thus, the second stage tail gas is passed through indirect heat exchanger 116 and cooled to a temperature of from about 100–300° F. to condense out most of the water vapor and some of the hydrocarbons as liquid and the gas-liquid mixture passed into gas-liquid separator 120 via line 118. The condensed hydrocarbon liquid is removed from the separator via line 122 and sent to further processing, while the second stage water containing ammonia and other water soluble compounds is removed from the separator via line 124 and passed to line 14, where it is combined with the offgas solution from the first stage reactor, and passed into vessel 12. The remaining tail gas removed from the separator via line 126 contains unreacted $H_2$ and CO, along with methane, nitrogen and $CO_2$, may be used as low value fuel or passed into vessel 12 or into the syngas generator 20.

The hydrocarbons produced by an HCS process according to the invention are typically upgraded to more valuable products, by subjecting all or a portion of the $C_{5+}$ hydrocarbons to fractionation and/or conversion. By conversion is meant one or more operations in which the molecular structure of at least a portion of the hydrocarbon is changed and includes both noncatalytic processing (e.g., steam cracking), and catalytic processing (e.g., catalytic cracking) in which a fraction is contacted with a suitable catalyst. If hydrogen is present as a reactant, such process steps are typically referred to as hydroconversion and include, for example, hydroisomerization, hydrocracking, hydrodewaxing, hydrorefining and the more severe hydrorefining referred to as hydrotreating, all conducted at conditions well known in the literature for hydroconversion of hydrocarbon feeds, including hydrocarbon feeds rich in paraffins. Illustrative, but nonlimiting examples of more valuable products formed by conversion include one or more of a synthetic crude oil, liquid fuel, olefins, solvents, lubricating, industrial or medicinal oil, waxy hydrocarbons, nitrogen and oxygen containing compounds, and the like. Liquid fuel includes one or more of motor gasoline, diesel fuel, jet fuel, and kerosene, while lubricating oil includes, for example, automotive, jet, turbine and metal working oils. Industrial oil includes well drilling fluids, agricultural oils, heat transfer fluids and the like.

While the invention has been described in particular detail for an FBSG syngas generator using processed natural gas as the hydrocarbon feed to the generator, a slurry HCS unit, hydrolysis of the hydrogen cyanide in the syngas to ammonia, etc., the practice of the invention is not limited to these specific embodiments as those skilled in the art will know and appreciate. Thus, any suitable and convenient source of syngas, feed for the syngas generator and syngas generating process may be used, as may either fluid catalyst bed or fixed catalyst bed, non-slurry HCS processes.

It is understood that various other embodiments and modifications in the practice of the invention will be apparent to, and can be readily made by, those skilled in the art without departing from the scope and spirit of the invention described above. Accordingly, it is not intended that the scope of the claims appended hereto be limited to the exact description set forth above, but rather that the claims be construed as encompassing all of the features of patentable novelty which reside in the present invention, including all the features and embodiments which would be treated as equivalents thereof by those skilled in the art to which the invention pertains.

What is claimed is:

1. A gas conversion process which comprises generating a synthesis gas comprising $H_2$ and CO from a feed comprising hydrocarbon gas in a synthesis gas generator, contacting said synthesis gas with a hydrocarbon synthesis catalyst at reaction conditions effective to react said $H_2$ and CO and form hydrocarbons and reversibly deactivate said catalyst, rejuvenating said deactivated catalyst with a gas comprising hydrogen to form an offgas containing ammonia, dissolving said ammonia out of said offgas with water, and stripping said ammonia out of said water and into said generator, with said hydrocarbon feed gas, in which said ammonia is consumed and which produces clean water.

2. A process according to claim 1 wherein said synthesis gas contains HCN and $NH_3$.

3. A process according to claim 2 wherein said catalyst comprises a Fischer-Tropsch catalyst.

4. A process according to claim 3 wherein the concentration of said ammonia and hydrogen cyanide in said synthesis gas is reduced prior to contacting it with said catalyst.

5. A process according to claim 4 wherein, prior to contacting said synthesis gas with said hydrocarbon synthesis catalyst, most of said hydrogen cyanide in said synthesis gas is converted to ammonia, followed by dissolving said ammonia out of said synthesis gas with water to form an ammonia and cyanide reduced gas.

6. A process according to claim 5 wherein said water used for dissolving said ammonia out of said offgas is obtained by condensing water vapor from tail gas formed by said hydrocarbon synthesis reaction.

7. A process according to claim 6 wherein said cyanide is converted to ammonia by hydrogenation or hydrolysis.

8. A process according to claim 7 wherein said ammonia and cyanide concentration in said synthesis gas is reduced to less than 0.1 vppm prior to contacting said catalyst.

9. A process according to claim 8 wherein said combined total of said ammonia and cyanide in said gas is less than 50 vppb.

10. A process according to claim 9 wherein said hydrocarbon gas has a sulfur content of less than 1 vppm.

11. A process according to claim 10 wherein said hydrocarbon synthesis catalyst comprises a catalytic cobalt component.

12. A process according to claim 11 wherein said hydrocarbon synthesis reaction occurs in a hydrocarbon synthesis slurry comprising particles of said catalyst and bubbles of said synthesis gas in a hydrocarbon liquid and wherein said liquid comprises hydrocarbon products of said synthesis which are liquid at said reaction conditions.

13. A process according to claim 11 wherein at least a portion of said synthesized hydrocarbons are upgraded by one or more conversion operations.

14. A process according to claim 12 wherein said cyanide is hydrolyzed to ammonia.

15. A gas conversion process which comprises:
   (a) producing, from a feed which comprises a sulfur reduced hydrocarbon gas, a synthesis gas comprising a mixture of $H_2$ and CO and which also contains ammonia and hydrogen cyanide, in a synthesis gas generator comprising a reaction zone for forming said synthesis gas;
   (b) contacting said synthesis gas with water in a high energy contacting means and separating said water from said gas;

(c) converting said most of said cyanide in said separated gas produced in step (b) to ammonia to form a cyanide reduced gas containing water vapor and ammonia;

(d) cooling said cyanide reduced gas to condense out a portion of said vapor as an aqueous solution of said ammonia to form a synthesis gas reduced in ammonia;

(e) scrubbing said ammonia reduced gas with water to dissolve more ammonia out of said gas to form a synthesis gas further reduced in ammonia;

(f) contacting said synthesis gas produced in step (e) with a hydrocarbon synthesis catalyst and reacting said $H_2$ and CO in the presence of said catalyst at reaction conditions effective to form hydrocarbons and reversibly deactivate said catalyst;

(g) contacting said catalyst with a gas comprising hydrogen to rejuvenate it and produce a rejuvenation offgas containing ammonia;

(h) contacting said offgas with water to dissolve said ammonia out of said gas and form an aqueous ammonia solution and separating said solution from said offgas, and (i) stripping said ammonia out of said water and into said generator, with said hydrocarbon gas, in which said ammonia is consumed in said reaction zone and which produces clean water.

16. A process according to claim 15 wherein at least a portion of said clean water is used to scrub said ammonia reduced synthesis gas in step (e).

* * * * *